United States Patent [19]

Puvilland

[11] Patent Number: 5,110,513
[45] Date of Patent: May 5, 1992

[54] PROCESS FOR PRODUCING AN ARTICLE MADE OF RESIN BY PHOTOPOLYMERIZATION AND APPLICATIONS OF THIS PROCESS

[75] Inventor: Gabriel Puvilland, Le Chesnay, France

[73] Assignee: Framatome, Courbevoie, France

[21] Appl. No.: 368,394

[22] PCT Filed: Sep. 9, 1988

[86] PCT No.: PCT/FR88/00445

§ 371 Date: May 11, 1989

§ 102(e) Date: May 11, 1989

[87] PCT Pub. No.: WO89/02358

PCT Pub. Date: Mar. 23, 1989

[30] Foreign Application Priority Data

Sep. 11, 1987 [FR] France ............... 87 12645

[51] Int. Cl.⁵ .............. A61C 13/087; B29C 35/08; B29C 39/40
[52] U.S. Cl. .................. 264/19; 156/272.8; 156/273.3; 156/275.5; 156/307.1; 250/492.1; 264/22; 264/250; 264/331.18; 264/331.21; 433/228.1
[58] Field of Search ............... 264/19, 22, 236, 250, 264/259, 264, 265, 331.18, 331.21; 156/273.3, 273.5, 275.5, 289, 272.8, 307.1; 250/492.1; 433/228.1

[56] References Cited

U.S. PATENT DOCUMENTS

| | | | |
|---|---|---|---|
| 2,491,097 | 12/1949 | Feagin | 264/19 |
| 3,254,411 | 6/1966 | Shelley | 433/217.1 |
| 4,234,310 | 11/1980 | Leuthard | 433/228.1 |
| 4,267,133 | 12/1981 | Kohmura et al. | 264/22 X |
| 4,764,118 | 8/1988 | Touati et al. | 433/228.1 X |
| 4,822,536 | 4/1989 | Voinis et al. | 264/22 |

FOREIGN PATENT DOCUMENTS

| | | |
|---|---|---|
| 77741 | 4/1983 | European Pat. Off. |
| 226123 | 6/1987 | European Pat. Off. |
| 1105159 | 11/1955 | France |
| 2381518 | 9/1978 | France |
| WO86/5085 | 9/1986 | PCT Int'l Appl. |
| 835311 | 5/1960 | United Kingdom |
| 2016994 | 9/1979 | United Kingdom |

*Primary Examiner*—Leo B. Tentoni
*Attorney, Agent, or Firm*—Pollock, Vande Sande & Priddy

[57] ABSTRACT

The part (3) is made, in a non-polymerized form, by juxtaposition of a major volume (4) at least equal to 80% of the total volume of the part (3) and of a complementary volume (5). First, the photopolymerization of the major volume (4) is carried out. Then, the photopolymerization of the complementary volume (5) is carried out, the major volume (4) and the complementary volume (5) being held in contact. The method applies particularly to restorative dentistry.

21 Claims, 1 Drawing Sheet

PROCESS FOR PRODUCING AN ARTICLE MADE OF RESIN BY PHOTOPOLYMERIZATION AND APPLICATIONS OF THIS PROCESS

FIELD OF THE INVENTION

The invention relates to a process for producing an article made of resin by photopolymerization, with a low degree of shrinkage, and to applications of this process, in particular in the field of restoration of teeth and of dental and surgical prostheses.

BACKGROUND OF THE INVENTION

Composite plastic resins whose curing is ensured by photopolymerization are increasingly being employed as materials for filling, adhesive bonding, coating or impressing, and for other uses where their ease and quickness of use may be a decisive advantage.

In particular, in the field of restorative dentistry and of dental prostheses, such photopolymerizable resins are more and more frequently employed instead of materials of metallic type.

Similarly, in the field of bone surgery, these materials are increasingly employed for bone restoration or for the manufacture of prostheses.

These composite plastic resins generally consist of monomers or of a prepolymer which are mixed with a diluent to adjust its fluidity and with various additives promoting the photopolymerization. To this mixture, which forms the matrix of the composite resin, there is added a variable proportion, depending on the desired characteristics, of filler consisting of very fine grains or fibers of quartz, silica, and the like, intended to increase the mechanical properties (hardness, strength) of the composite resin.

In all these applications, and in particular when the polymerization must be performed in situ, the flexibility and the speediness of photopolymerization, i.e., polymerization under the effect of luminous radiation, constitute valuable advantages and make the practitioner's task easier.

The use of luminous sources of high photopolymerization performance, insofar as photopolymerization is concerned, particular of the argon laser, has made it possible to broaden the field of application and the practical possibilities of the use of this process.

However, the polymerization of composite resins is always accompanied by a volume shrinkage which results in major disadvantages and limits the performance of polymerizable resins in many applications.

This is so in the case of dental or bone restoration, where polymerization shrinkage can give rise to stresses which are capable of inducing pain in the patient or causing a certain deterioration of the prostheses, such as fissures, opening the way to bacterial infections.

In the case of other applications, and in particular in the case of the manufacture or of the assembly of highly precise industrial components, polymerization shrinkage makes it difficult to maintain accurate dimensions and gives rise to the appearance of fissures or of separations, in particular in the connecting regions between the components.

SUMMARY OF THE INVENTION

The object of the invention is a process for producing an article made of composite resin by photopolymerization, consisting in using at least one resin in an unpolymerized deformable state and then producing its polymerization under the effect of luminous radiation, with a very low polymerization shrinkage.

To this end:

the article is formed by juxtaposition of a main volume, equal to at least 80% of the total volume of the article, of a resin-based first photopolymerizable material and of a complementary volume of a resin-based second photopolymerizable material, and the photopolymerization of the main volume of photopolymerizable material is produced in a first step and the photopolymerization of the complementary volume of photopolymerizable material is produced in a second step, the main volume and the complementary volume being maintained in contact in an assembly position.

BRIEF DESCRIPTION OF THE DRAWINGS

In order that the invention may be more clearly understood, a description will now be given, by way of example, and with reference to the appended drawings, of an embodiment of the process according to the invention, in the case of the repair of a tooth by producing inside a dental cavity.

DESCRIPTION OF PREFERRED EMBODIMENT

Figure 1:
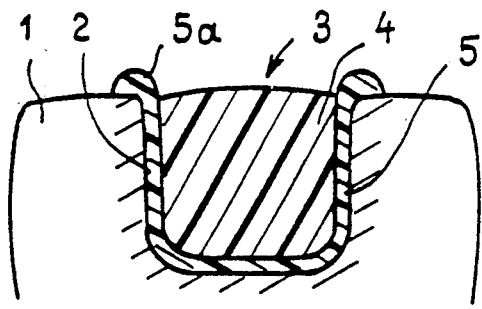
FIG. 1 is a sectional view of the dental cavity and of its filling component, before photopolymerization.

FIG. 1 shows a tooth 1 exhibiting a cavity 2 which it is intended resin whose molding and polymerization will be carried out directly in the cavity 2.

Cavity 2 is cleaned and milled using a bur in the usual manner, before the component 3 is placed in position in an unpolymerized and, consequently, relatively fluid and deformable form.

The consistency of the photopolymerizable mixture is generally that of a very soft paste.

According to the invention, the filling component 3 consists of a juxtaposition of a main volume 4 of a first photopolymerizable material consisting of a mixture and of a complementary volume 5 of a second photopolymerizable material consisting of a mixture which is different from the mixture constituting the main volume 4.

Preferably, and as shown in FIG. 1, the complementary volume 5 forms a continuous thin layer covering the whole of the wall of the cavity 2, the main volume 4 forming the central part and the outer surface of the filling component 3.

Figure 2:
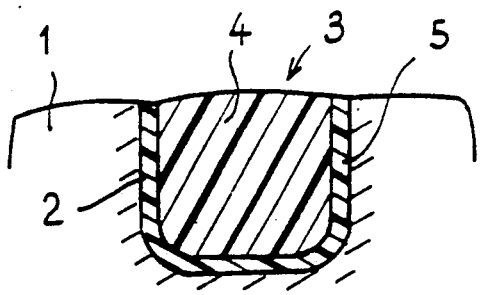
FIG. 2 is a sectional view similar to FIG. 1 of the dental cavity after photopolymerization.

The main volume 4 of the filling component 3 represents substantially 90% of the total volume of the definitive component such as shown in FIG. 2.

The complementary volume 5 represents slightly more than 10% of the total volume of the component 3 and, for example, substantially 11% of this total volume. The excess material of the complementary volume 5 forms a small reserve ridge 5a on the edge of the cavity 2.

In a first embodiment of the process according to the invention, the main volume 4 of the component 3 is reconstituted with a first photopolymerizable material consisting of a mixture which is sensitized so that its photopolymerization takes place when this mixture is exposed to a laser radiation which has a first wavelength λ1.

The complementary volume 5 consists of a photopolymerizable mixture which is insensitive to the laser radiation of wavelength λ1 and whose photopolymerization takes place under the effect of a laser radiation of wavelength λ2.

After the cavity 2 has been filled with the component 3 constituted as described above, the main volume 4 of the component 3 is exposed to a laser radiation of wavelength λ1, for example of a radiation originating from an argon laser. This radiation produces the polymerization of the main volume 4, whose outer surface remains in contact with the external complementary volume 5. The fluidity of the unpolymerized material forming the complementary volume 5 is such that this material ensures that the main volume 4 is sustained, while it remains continuously in an intimate contact with the outer surface of this volume 4 throughout its surface.

During its curing by photopolymerization and after curing, the main volume 4 is in the situation of a free body in a viscous mass.

The polymerization shrinkage of the main body 4 is therefore automatically compensated by the material of the complementary volume 5 whose fluidity is sufficient for this material to follow the movements of the surface of the component 4 during its shrinkage and to fill any cavity of very small volume which may be produced by such shrinkage.

When the polymerization and the shrinkage of the main volume 4 have been completed, the major part of the reserve of material 5a which has been used to compensate the shrinkage has entered inside the cavity 2.

The complementary volume 5 of polymerizable material is then exposed to the laser radiation of wavelength λ2, to obtain the photopolymerization of this complementary volume and the adhesive bonding of the whole filling to the wall of the cavity, the complementary volume being in contact with the main volume in its assembly position and with the wall of the cavity 2 in the tooth 1.

The adhesiveness of the complementary volume to the wall of the cavity can be improved by etching this wall before the cavity is filled with the component in the unpolymerized state.

The shrinkage of the complementary volume 5 is of very low absolute value, since the volume 5 itself represents a small fraction of the total volume of the component 3.

This results in both perfect bonding between the filling component 3 and the walls of the cavity 2, and substantially zero stresses in the tooth, in the filling component and at the interface of the two.

A quantity of reserve material 5a which is slightly greater than the predictable shrinkage of the main volume 4 of the component 3 can be employed and, in this case, the excess material of the part 5 of the component 3 is removed and levelled off with the bur after the volume 5 has cured.

A complementary volume can be provided, whose photopolymerization will be ensured in a second step, representing more than 10% of the total volume of the component.

However, this complementary volume must not be too great, so that its uncompensated final shrinkage remains within acceptable limits.

This is the reason why the main volume is chosen so as to form at least 80% of the total volume of the component.

Since the linear shrinkage of the resins usually employed in dentistry, such as the resins shown below, is from 0.2 to 1%, the uncompensated final shrinkage of the component is thus limited in all cases to a value which is smaller than the shrinkage which had to be accepted in a process according to the prior art and in the best of cases.

To produce the filling of a dental cavity by means of the process as described, the composition given below was employed to form the main volume 4 of the filling component. In the case of the matrix:

3.20% of benzoin methyl ether (initiator)
1.75% of methyldiethanolamine (accelerator)
0.05% of eosin (sensitizer)
95% of base resin consisting of a mixture of BIS-GMA (bisphenol A bis(2-hydroxypropyl) methacrylate) monomer and of TEGDMA (triethylene glycol dimethacrylate) diluent in equal parts. The filler consisted of 200-μm quartz particles and represented 80% by weight of the composite resin.

All of the percentages given above are percentages by weight.

The simultaneous use of an initiator and of eosin in the mixture makes it possible to obtain fast polymerization of the photopolymerizable mixture when the latter is exposed to radiation originating from an argon laser tuned to a wavelength of 514 nm.

The following composition was employed to produce the complementary volume 5 of the filling component. In the case of the matrix:

0.3% of camphoroquinone (photoinitiator)
1.0% of methyldiethanolamine (accelerator)
98.7% of base resin filled with a composition identical with that shown in the case of the main volume.

In the case of the filler: nature and proportion identical with those of the main volume.

These percentages are percentages by weight.

By employing camphoroquinone as the photoinitiating agent, a photopolymerizable mixture is obtained whose polymerization is ensured by exposure to the radiation of an argon laser tuned to a wavelength of 488 nm.

To implement the process, a monochromatic argon laser which is tuned successively to wavelengths of 514 nm and 488 nm was employed as a source of radiation of the photopolymerizable resins.

In each case, the most intense wavelengths situated in the neighborhood of 514 nm, and 488 nm respectively, will ensure the photopolymerization of the corresponding photopolymerizable mixture forming the main volume or the complementary volume of the filling component.

Instead of the additives shown above, which permit the photopolymerization of the mixture at the wavelengths shown, it is possible to employ other additives, such as:

as initiator:
a benzoin alkyl ether
an acetophenone derivative
benzoin oxime
benzophenone
as sensitizer:

ethyleosin at 532 nm
erythrosin at 525 nm
methylene blue at 632 nm
as photoinitiator, at 488 nm:
para-benzoquinone or any diketone
as accelerator (all wavelengths):
methyldiethanolamine
methylethanoldiamine
N,N-dimethylaminoethyl methacrylate
tertiary amines.

In all cases, the substance employed as an initiator represents from 0 to 15% of the total mass of the resin before incorporation of the filler (matrix), the sensitizer from 0 to 1%, the photoinitiator from 0 to 10% and the accelerator from 0 to 15%.

Similarly, instead of the composite resins shown above, it is possible to employ:

as a monomer or prepolymer forming the organic matrix, any mono- or polyfunctional methacrylate resins, especially:
methyl methacrylate (MMA)
bisphenol A dimethacrylate
ethylene glycol dimethacrylate
trimethylolpropane trimethacrylate (TMPTMA)
urethane dimethacrylate (UEDMA)

as an associated filler strengthening the mechanical properties: particles from 0.01 to 200 μm or fibres from 200 μm to 5 mm of quartz, silica, glasses, polymers, ground or synthesised of single or mixed particle size, coated, before incorporation into the matrix and in order to improve the bonding therewith, with a coupling product containing dipolar molecules such as organosilanes.

It is also possible to perform the two successive photopolymerizations employed in the process according to the invention at a single wavelength. In this case, a polymerization retarder consisting, for example, of hydroquinone derivatives such as hydroquinone dimethyl ether, or of phenol derivatives such as aminophenol, will be added to one of the resin-based photopolymerizable mixtures.

In all cases, the substance employed as a retarder represents from 0.01 to 0.10% by weight of the resin before the filler is incorporated (matrix).

This photopolymerizable mixture containing a retarder is intended to form the complementary volume of the component.

After the cavity has been filled with the filling component consisting of the juxtaposition of the mixture of resin without retarder and with a polymerization retarder, the filling component is exposed to radiation of a suitable wavelength. The photopolymerization of the mixture forming the main volume 4 will take place in a first step, and the photopolymerization of the resin to which a retarder has been added and which forms the complementary volume, in a second step.

While the main volume of the component is polymerizing, it is possible to compensate the shrinkage of this volume with the fluid mixture forming the unpolymerized complementary volume.

Figure 3:
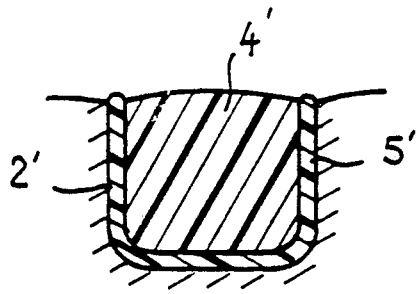
FIGS. 3, 4 and 5 are sectional views of the dental cavity during three successive stages of the process for producing the filling component, which is carried out according to an alternative form of embodiment.
Figure 4:
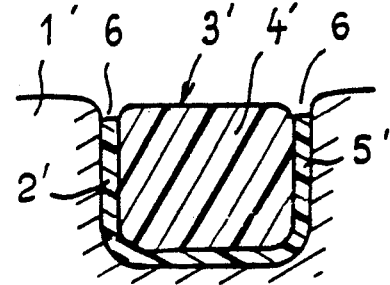
Figure 5:
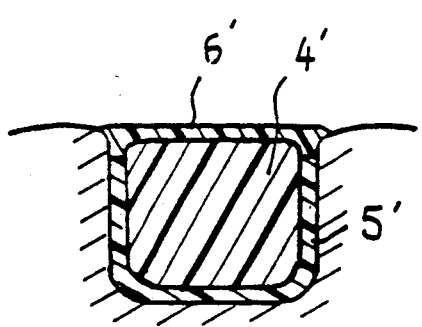

An alternative embodiment of the process can be seen in FIGS. 3, 4 and 5, the complementary volume 5' occupying at the initial instant (FIG. 3) precisely the volume remaining in the cavity 2' around the main volume 4'.

After photopolymerization of the main volume 4' (FIG. 4), the resin of volume 5' which has been used to compensate the shrinkage of the main volume 4' has entered the cavity 2', so that after photopolymerization of the complementary volume 5' the shrinkage of this volume is accompanied by the appearance of a hollow part 6 of the component 3', in relation to the tooth 1'.

This hollow part 6 can be filled with a stopping material 6' deposited onto the component 3' after it has cured by polymerization. The layer 6' may also consist of a photopolymerizable resin whose curing is ensured by exposure to laser radiation.

Figure 6:
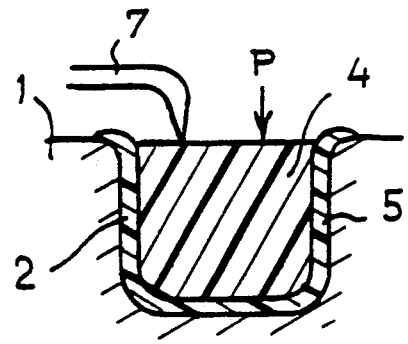
FIG. 6 is a sectional view of the dental cavity during the final stage of implementation of the process according to the invention and according to a second alternative form.

FIG. 6 shows an alternative embodiment of the process, where the bringing of the main volume 4 of the filling component 3 into contact with the complementary volume 5, in their assembly position inside the cavity 2, while the complementary volume 5 is being photopolymerized, is ensured by a pressure P exerted by a tool 7 pressing on the main volume 4 of the component 3, after its curing by polymerization.

The photopolymerization of the main volume of cavity filling can also be carried out before placing in position the complementary volume of the component forming the layer for adhesive bonding and for compensating the polymerization shrinkage. To do this, the wall of the cavity 2 is prepared before filling so as to prevent the adhesive bonding of the main volume during its polymerization. For example, a suitable substance such as an oil can be applied to the wall. The cavity is then completely filled with a photopolymerizable material forming the main volume of the repair component. Curing of the main volume is carried out in situ by photopolymerization, as described above. The main volume is then easily extracted from the cavity by virtue of its shrinkage and in the presence of an oily product preventing the adhesive bonding to the cavity wall. Care must be taken before filling to shape the cavity so as to avoid any mechanical blocking of the component. The cavity wall is then cleaned and, if desired, etched. A complementary volume of the polymerizable material is applied to the wall and the main volume is placed in position in an assembly contact with the complementary volume. The photopolymerization of the complementary volume, which ensures both the compensation for the shrinkage and the adhesive bonding of the main volume, is then carried out.

The process according to the invention can be used not only in the restoration of teeth filling components positioned and photopolymerized in dental cavities, but also in the manufacture of dental prostheses, inside impressions or molds.

In this case, the impression or mold acts as the dental cavity whose filling is ensured, as described above.

The process according to the invention can also be applied in the context of restorative surgery, for partial reconstruction of certain bones, and in the production of complete bone prostheses.

The process according to the invention can also find many applications within the scope of the manufacture of articles made of plastic resin which must have a very high degree of accuracy of shape and dimension. In this case, the compensation for most of the polymerization shrinkage, while the article is being molded and cured, enables a very high dimensional accuracy to be obtained. The process according to the invention is therefore capable of many applications in various industries employing resin components and, in particular, in the field of electronics.

I claim:

1. Process for producing an article made of resin based, photopolymerizable materials by photopolymerization with a low degree of shrinkage, comprising the steps of:

(a) juxtaposing and maintaining in contact a main volume, equal to at least 80% of a total volume of said article, of a resin based, unpolymerized, first photopolymerizable material which is photpolymerizable to radiation at a first wavelength and a complementary volume of a resin based, unpolymerized, second photopolymerizable material which is photopolymerizable to radiation at a second wavelength, but which is insensitive to, and not photopolymerizable at, radiation at said first wavelength;

(b) photopolymerizing said first photopolymerizable material of said main volume by applying radiation at said first wavelength to polymerize said first photopolymerizable material in said main volume, while said second photopolymerizable material in said complementary volume is unpolymerized and compensates for any shrinkage of said first photopolymerizable material, said main volume and said complementary volume being maintained in contact; and then (c) photopolymerizing said second photopolymerizable material of said complementary volume by applying radiation at said second wavelength to polymerize said second photopolymerizable material in said complementary volume to join said main and complementary volumes and produce said article.

2. Process according to claim 1, wherein said complementary volume (5) consists of a photopolynmerizable material indentical with the material forming said main volume (4), to which a polymerization retarder has been added, said component (3) being exposed to luminous radiation ensuring photopolymerization of the photopolymerizable material forming said main volume (4) and said complementary volume (5).

3. Process according to claim 1, wherein photopolymerization of said main volume (4) is carried out before said main volume is brought into contact with said complementary volume (5).

4. Process according to claim 1, wherein the photopolymerizable materials are in the form of a composite material comprising a base resin mixture of monomers or prepolymers, a diluent for adjusting viscosity, a reinforcing filler and photopolymerization additives.

5. Process according to claim 4, wherein said resin is a mono or polyfunctional methacrylate resin.

6. Process according to claim 5, wherein the monomer or prepolymer resin consists of at least one substance selected from the group consisting of
BIS-GMA
methyl methacrylate (MMA)
bisphenol A dimethacrylate
ethylene glycol dimethacrylate
trimethylolpropane (TMPTMA), and
urethane dimethacrylate (UEDMA).

7. Process according to claim 4, wherein the filler for reinforcing the resin consists of at least one substance selected from the group consisting of quartz, silica, glasses and polymers in the form of particles from 0.01 to 200 μm and in the form of fibers from 200 μm to 5 mm in length.

8. Process according to claim 4, wherein said photopolymerization additives comprise at least one initiator, at least one sensitizer and at least one accelerator, in proportions not exceeding 15%, 1% and 15%, respectively, of a total mass of photopolymerizable material.

9. Process according to claim 8, wherein the initiator consists of a substance selected from the group consisting of
benzoin methyl ether,
a benzoin alkyl ether,
an acetophenone derivative,
benzoin oxime, and
benzophenone,
and the sensitizer is selected from the group consisting of
eosin,
ethyleosin,
erythrosin, and
methylene blue.

10. Process according to claim 4, wherein the photopolymerization additives comprise at least one photoinitiator and an accelerator in respective proportions not exceeding 10% and 15% of the total mass of photopolymerizable material.

11. Process according to claim 10, wherein the photinitiator consists of at least one substance selected from the group consisting of
camphoroquinone,
para-benzoquinone, and
a diketone.

12. Process according to claim 8, wherein the accelerator consists of at least one substance selected from the group consisting of
methyldiethanolamine,
methylethanoldiamine,
N,N-dimethylaminoethyl methacrylate, and
a tertiary amine.

13. Process according to claim 1, wherein photopolymerization of said main volume (4) is carried out with a first laser and photopolymerization of said complementary volume (5) with a second laser.

14. Process according to claim 1, wherein photopolymerization of said main volume (4) and photopolymerization of said complementary volume (5) are carried out with a laser adapted to be adjusted to two different wavelengths.

15. Process according to claim 14, wherein said laser is an argon laser adjustable to two principal wavelengths at 488 and 514 nm.

16. Use of the process according to any one of claims 1 to 15, to restoration of a tooth (1) exhibiting a dental cavity (2), wherein the resin component is a component for filling (3) said cavity (2) produced by molding and photopolymerization, the photopolymerization of said complementary volume (5) additionally ensuring adhesive bonding of the whole component to said tooth (1).

17. Use of the process according to claim 2 or 1, in restoration of a tooth (1) exhibiting a detail cavity (2), wherein said component (3) is a component for filling said cavity (2), produced be molding in situ in said cavity a component comprising a main volume (4) and a complementary volume (5) in an unpolymerized state and then by in situ polymerization of said main volume and said complementary volume.

18. Use of the process according to claim 17, wherein said complementary volume (5) of said component (3) in the unpolymerized state forms a reserve (5a) overflowing in relation to a surface of said tooth (1) to compensate shrinkage of said main volume (4) of said component (3), while said component is polymerizing.

19. Use according to claim 17, wherein, after polymerization of said complementary volume (5) of said filling component (3), stopping (6') of a hollow part (6) at a surface of said tooth (1), due to shrinkage of said main volume (4') and of said complementary volume (5') during their polymerization, is carried out.

20. Use according to claim 17, wherein during the polymerization of the complementary volume (5), a pressure P is applied to a filling component (3) towards an interior of said cavity (2) by pressing on the photopolymerized main volume (4).

21. Use of the process according to claim 3, in to restoration of a tooth exhibiting a dental cavity, comprising the steps of preparing a wall of said cavity to facilitate demolding of a component polymerized in situ, filling said cavity with a polymerizable material forming said main volume of said component, carrying out photpolymerization of said main volume, demolding said polymerized main volume, preparing said cavity wall to promote bonding of a polymerized component, introducing said complementary volume of said component in the unpolymerized state into the cavity, in contact with said wall, reintroducing said main volume into said cavity, and carrying out photopolymerization of said complementary volume in contact with the polymerized main volume whose adhesive bonding to the tooth is thus ensured.

* * * * *